United States Patent
Fuerst et al.

(10) Patent No.: US 11,950,850 B2
(45) Date of Patent: Apr. 9, 2024

(54) FEEDBACK FOR SURGICAL ROBOTIC SYSTEM WITH VIRTUAL REALITY

(71) Applicant: Verb Surgical Inc., Santa Clara, CA (US)

(72) Inventors: Bernhard Fuerst, Sunnyvale, CA (US); Eric Johnson, Pacific Grove, CA (US); Pablo Garcia Kilroy, Menlo Park, CA (US)

(73) Assignee: Verb Surgical Inc., Santa Clara, CA (US)

(*) Notice: Subject to any disclaimer, the term of this patent is extended or adjusted under 35 U.S.C. 154(b) by 0 days.

(21) Appl. No.: 17/486,471

(22) Filed: Sep. 27, 2021

(65) Prior Publication Data

US 2022/0008133 A1 Jan. 13, 2022

Related U.S. Application Data

(63) Continuation of application No. 16/870,586, filed on May 8, 2020, now Pat. No. 11,166,765.

(51) Int. Cl.
| | | |
|---|---|---|
| *A61B 34/10* | (2016.01) | |
| *B25J 13/06* | (2006.01) | |
| *G06F 3/0481* | (2022.01) | |
| *G06F 3/04815* | (2022.01) | |

(52) U.S. Cl.
CPC ............... *A61B 34/10* (2016.02); *B25J 13/06* (2013.01); *G06F 3/04815* (2013.01); *A61B 2034/104* (2016.02); *A61B 2034/105* (2016.02)

(58) Field of Classification Search
CPC .............. A61B 34/10; A61B 2034/104; A61B 2034/105; B25J 13/06; G06F 3/04815
See application file for complete search history.

(56) References Cited

U.S. PATENT DOCUMENTS

| | | | |
|---|---|---|---|
| 2010/0211897 A1 | 8/2010 | Cohen et al. | |
| 2010/0234857 A1* | 9/2010 | Itkowitz ............... | G09B 23/285 |
| | | | 700/259 |
| 2013/0245375 A1 | 9/2013 | DiMaio et al. | |
| 2014/0018960 A1 | 1/2014 | Itkowitz | |
| 2017/0049517 A1 | 2/2017 | Felder et al. | |
| 2017/0319282 A1 | 11/2017 | Jarc et al. | |
| 2018/0098813 A1 | 4/2018 | Nesichi et al. | |
| 2018/0168750 A1* | 6/2018 | Staunton ................. | A61B 34/76 |
| 2018/0233222 A1* | 8/2018 | Daley .................... | G16H 50/50 |
| 2018/0324539 A1 | 11/2018 | Lovitt | |
| 2020/0038124 A1 | 2/2020 | Lin et al. | |
| 2020/0069377 A1* | 3/2020 | Finley .................... | A61B 90/37 |
| 2020/0074402 A1 | 3/2020 | Adato et al. | |
| 2020/0275976 A1* | 9/2020 | Mckinnon ............ | A61B 5/0077 |
| 2020/0297440 A1* | 9/2020 | Forstein ............. | A61G 13/0063 |
| 2020/0405396 A1* | 12/2020 | Mcguan ................. | G16H 50/50 |

OTHER PUBLICATIONS

Non-Final Office Action for U.S. Appl. No. 16/667,241 dated Apr. 27, 2021, 17 pages.
Non-Final Office Action for U.S. Appl. No. 16/667,237 dated Mar. 31, 2021, 17 pages.

* cited by examiner

*Primary Examiner* — Michelle Chin
(74) *Attorney, Agent, or Firm* — Aikin & Gallant, LLP

(57) ABSTRACT

A virtual surgical robot being built from kinematic data is rendered to a display. A user input is received to effect a movement or a configuration of the virtual surgical robot. The kinematic data is modified based on evaluation of the movement or the configuration of the virtual surgical robot.

20 Claims, 4 Drawing Sheets

FEEDBACK FOR SURGICAL ROBOTIC SYSTEM WITH VIRTUAL REALITY

CROSS-REFERENCE TO RELATED APPLICATIONS

This application is a continuation of U.S. patent application Ser. No. 16/870,586 filed May 8, 2020, which is incorporated by reference herein in its entirety.

TECHNICAL FIELD

This invention relates generally to surgical robotic systems, and more specifically to systems and methods to provide feedback using a virtual reality system.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A surgical robotic arm may, for example, support at its distal end various devices such as surgical end effectors, imaging devices, cannulas for providing access to the patient's body cavity and organs, etc. Thus, a surgical robotic arm can assist in performing surgery.

Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

SUMMARY

Development of surgical robotic arms can be difficult and costly. Surgical robotic arms can have multiple movable members, sensors, encoders, actuators and mounting hardware. Each surgical robotic arm can assume countless different poses. Due to the complexity of such a system, development carries risk in that it may be difficult to determine the final design without knowing whether a surgical robotic arm and tool can reach and move within a surgical workspace in a manner required by a particular real surgical procedure (e.g., laparoscopic surgery).

Early feedback can be beneficial for design, proof, and/or testing of a surgical robotic system (e.g., surgical robotic arms, surgical tool, platform, user console, control tower, etc.). Early feedback through simulation and virtualization can inform critical design decisions without implementing physical hardware (e.g., physical mock-ups and prototypes of a surgical robotic arm). Through a virtual reality simulation, feedback can be provided early and often, on various design aspects of the surgical robotic system and with respect to performance of such a system during one or more surgical procedures. This can save cost in development of such systems, reduce errors, and optimize design in an efficient manner.

Workflow of surgical procedures can also be improved. A workflow can include a pre-defined series of steps and pre-defined surgical equipment and placement thereof, for preparing for and performing surgical procedures. Workflows can vary between procedures and equipment models. By simulating procedure workflows with virtual surgical robotic systems (e.g., during a development phase), analysis of the simulation can determine which steps of a workflow may be modified, and whether aspects of the surgical robotic system (e.g., a surgical robotic arm, tool or platform) can be modified and improved. Such aspects can include increasing a length of a surgical robotic arm, adding or removing degrees of freedom, modifying a shape, or increasing a reach. In some cases, analysis of the simulation may determine that additional controls may be helpful for a surgical procedure. For example, it may be determined that a table remote control should allow a user to adjust the table's tilt, height, or shift the table from side to side, or adjust robotic arms through commands, such as 'stow', 'un-stow', 'park', and 'move arms away'.

Simulated virtual surgical procedures can provide immediate feedback and evaluation of a surgical robotic system, including robot design. The evaluation can be based on tracked movement of the user and the virtual surgical robotic system. Simulation sessions can test and score the user's ability to perform the procedure and evaluate the design and compatibility of a surgical robotic system.

In one embodiment, a virtual reality feedback system for development of a surgical robotic system includes a processor and a display. The processor is configured to render on the display a virtual surgical robot, which can be immersed in a virtual environment. The virtual surgical robot is built, virtually, based on kinematics data that defines geometry and movement of the robot. The processor can effect movement or configuration of the virtual surgical robot based on user input. The kinematics data is modified based on the evaluation of the movement or the configuration.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosures.

Reference in the specification to "one embodiment" or "an embodiment" means that a particular feature, structure, or characteristic described in conjunction with the embodiment can be included in at least one embodiment of the disclosure. The appearances of the phrase "in one embodiment" in various places in the specification do not necessarily all refer to the same embodiment.

Figure 1:
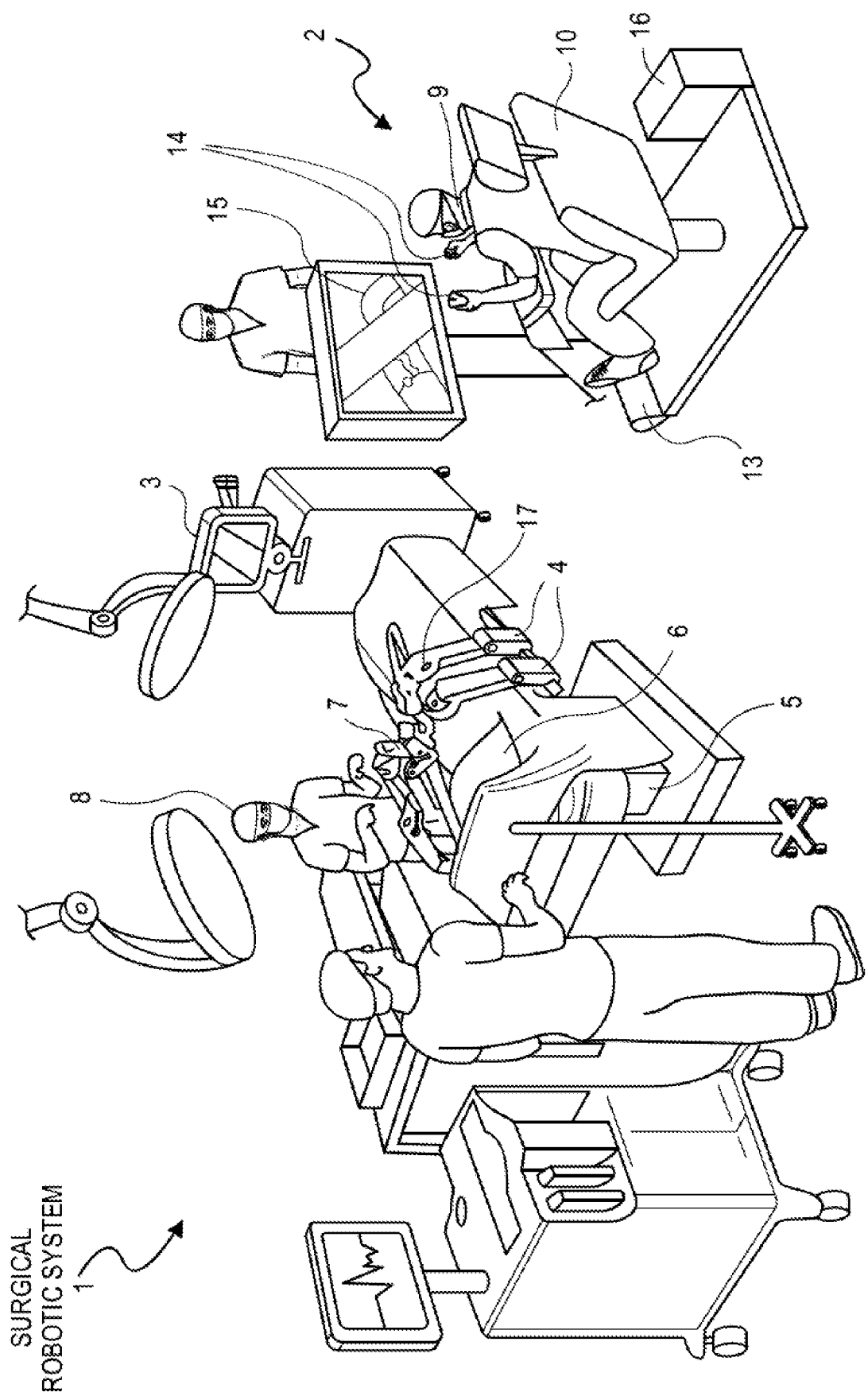
FIG. 1 illustrates a surgical robotic system according to one embodiment.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

A surgical robotic arm can have movable, jointed, and/or motorized members with multiple degrees of freedom that can hold various tools or appendages at distal ends. Example systems include the da Vinci(r) Surgical System which can be used for minimally invasive surgery (e.g., urologic surgical procedures, general laparoscopic surgical procedures, gynecologic laparoscopic surgical procedures, general non-cardiovascular thoracoscopic surgical procedures and thoracoscopically assisted cardiotomy procedures). A "virtual surgical robotic arm" can be a computer generated model of a robotic arm rendered over the captured video of a user setup. The virtual surgical robotic arm can be a complex 3D model of the real robotic arm. Alternatively or additionally, a virtual surgical robotic arm can include visual aids such as arrows, tool tips, or other representation relating to providing pose information about a robotic arm such as a geometrically simplified version of the real robotic arm.

Figure 2:
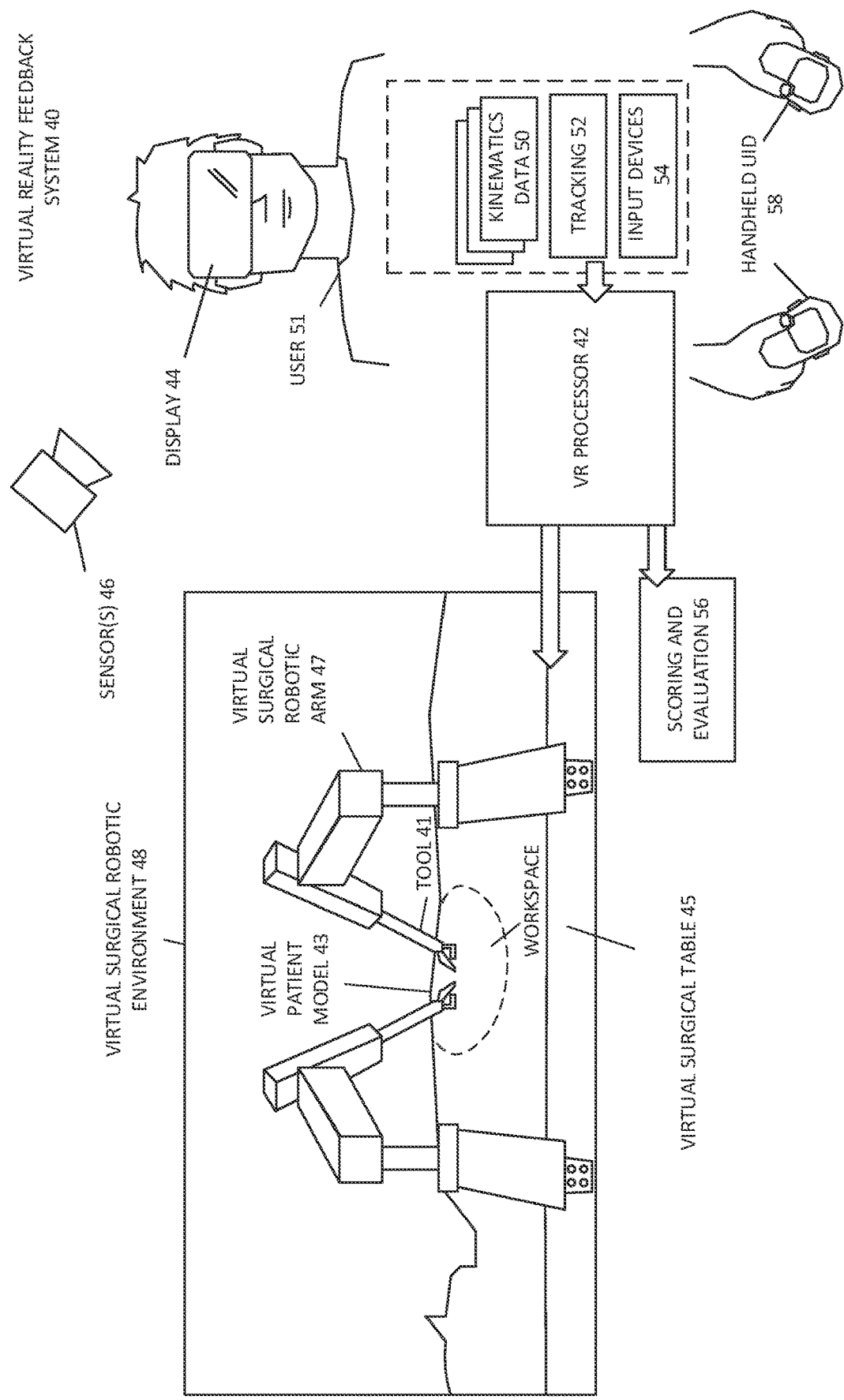
FIG. 2 shows system for generating a virtual surgical environment, according some embodiments.

Referring to FIG. 2, a virtual reality based feedback system 40 is shown that can improve development of a surgical robotic system. The system can include a processor 42 and a display 44. The processor is configured to render on the display a virtual surgical environment 48 including a virtualized surgical robotic system like that shown in FIG. 1. A virtualized surgical robot can include one or more virtual surgical arms 47, a virtual surgical platform 45, and/or a virtual surgical tool 41. A virtual patient 43 can be positioned on the virtual surgical table. The processor can track a motion of a user and/or a movement of the virtual surgical robot in the virtual surgical environment. The environment can include a virtual operating room that includes geometrical features such as walls, ceiling height, and dimensions thereof. Virtual OR staff (e.g., assistants) can be generated and positioned in the virtual surgical environment, for example, based on workflow requirements.

The system can include one or more sensors 46 that provide tracking data 52 to the processor. The sensors can be used to track movement of the user 51. The sensors can include optical tracking devices, e.g., a 2D camera, 3D camera, IR cameras, electromagnetic tracking systems, or acoustic tracking systems using ultrasonic waves. In some embodiments, one or more of the sensors can be integral to a head worn device (e.g., a head mounted display (HMD) that is worn by the user. The HMD can provide 3D visualization using a 3D display or a pair of displays.

The system can, at block 56, evaluate the design of the surgical robotic system based on the tracked movement of the user and/or the movement of the virtual surgical robot. Evaluation can be based on a reach and/or access of the user or the reach and/or access of a virtual surgical robotic arm. For example, the system can determine that a user or virtualized personnel cannot reach critical components, the patient, or equipment required fora procedure or during set-up or tear-down. Evaluation can be based on whether movements of a surgical robotic arm and/or tool were adequately performed, or capable of reaching and moving in a workspace of a patient model, as required in a particular surgical procedure. One or more scores can be generated that grades the surgical robotic system based on reach, access, and/or movement in a surgical workspace.

Evaluation can account for predefined workflow stages (e.g., set-up, performance of a procedure, and/or tear-down). Workflow can include different stages that can require different positioning and arrangement of the surgical robotic components and personnel at each stage. For example, during a simulated procedure or other training session, a user can perform exercises that test a compatibility of the surgical robotic system with a workflow of a procedure. Based on evaluation of the movements of the virtual robotic system, positions of the virtual assistants, or movements of a user in the virtual environment, the processor can determine that the surgical robotic platform should have an elevation or tilt control to provide improved access to a surgical workspace in a patient model. In another example, based on the evaluation, the processor can determine that an additional degree of freedom in a surgical robotic arm may improve access of the surgical tool within the surgical workspace or improve stowing ability, or that a member of the surgical robotic arm can be lengthened or shortened. In yet another example, a component or the shape of the surgical robotic arm, tool, surgical table, or platform can be modified.

In some embodiments, input devices 54 can include a user interface or one or more handheld user input devices 58 that allow a user to move the virtual surgical robot in the virtual environment. The controls that translate movement and inputs from the handheld UIDs 58 to effect movement in the virtual surgical robot can mimic control of a surgical robotic system by handheld UIDs as shown and described in FIG. 1. Alternatively or additionally, virtual objects can be moved when the user touches, in virtual space, one or more regions of the virtual object (e.g., special points can be used to drag about the virtual objects in virtual space). This can provide input as to docking capabilities of a surgical robot, and positioning of various equipment as it relates to a workflow. Handheld user input devices 58 can have sensors (e.g., inertial measurement unit, gyroscope, accelerometers, etc.,) and/or buttons to receive inputs from the user. In some embodiments, the user can arrange a surgical robotic arm in different poses, move a patient model, change a height or pitch of a surgical table or platform, or move the surgical robotic arm or surgical tool, during a simulated session in the virtual environment. The input devices can include any user interface (e.g., a GUI) that allows the user to specify settings. Settings can include what configuration the virtual surgical robot takes on, for example, 2×2, 2×2 cross-under, or 3×1, as described in other sections.

In one embodiment, the processor is further configured to modify the virtual surgical robotic system, including modifying or re placing the virtual robotic arm, or the virtual operating table. Kinematic data 50 of the virtual surgical robotic system (e.g., URDF and/or CAD files of surgical robotic arms, platforms, tools, etc.) can be stored in one or more databases accessible to the VR processor. The models can include kinematic data (e.g., URDF files) that define movement and geometry of a robotic component such as a robot arm, surgical table/platform, or surgical tool, as described in other sections. In other words, the kinematic data can represent design of the robot. Based on constraints defined by the kinematic data, the processor can determine how each virtual robot can move in the virtual environment.

In one embodiment, the user is virtualized in the virtual surgical robotic environment. For example, if the user is wearing a HMD and looks down, the user might see a virtual rendering of the user's body. The virtual user can be rendered based on sensors 46 which can be set-up in the physical environment around the user, and/or located on the HMD.

In the absence of hardware and during the development of a surgical robotic system, development teams need the ability to make informed decisions about direction both from a hardware perspective as well as from a workflow perspective. A virtual reality process can provide precise insight into development of control software and hardware and allows for testing different configurations through different workflows.

Figure 3:
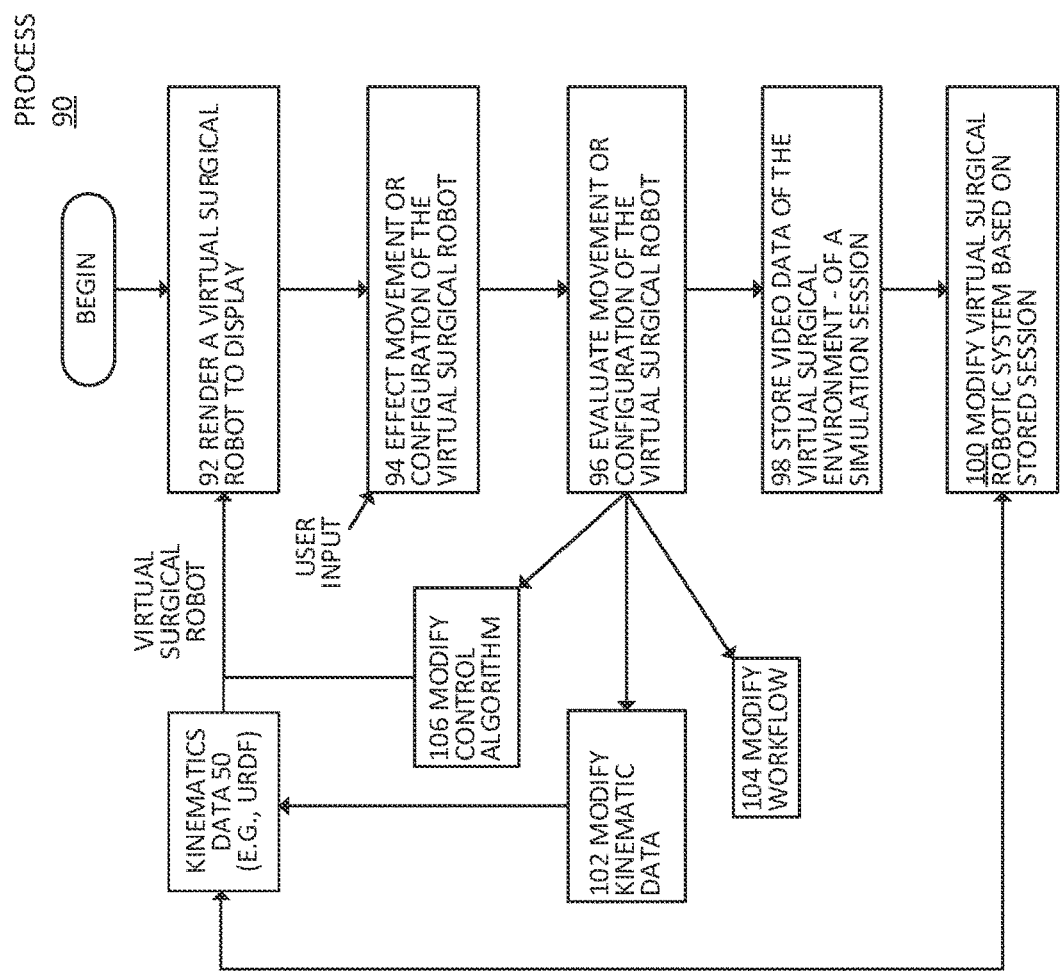
FIG. 3 shows a process for providing feedback of a surgical robotic system, according to some embodiments.

A process 90 is shown in FIG. 3 that provides feedback for development of a surgical robotic system. The process can be performed with the system described in FIG. 2. The process can begin based on user input. A surgical procedure type, workflow specifications, configuration of the virtual surgical robot, and other options such as patient size, can also be selected for the virtual exercise. In some embodiments, different prototypes of surgical robots can be selected and evaluated to guide development of the surgical robots and/or to validate a design prior to completion of hardware development and manufacturing.

At block 92, the process includes rendering a virtual surgical robot to a display. The virtual surgical robot can include at least one of a robotic arm, a surgical robotic table, and a surgical tool attachment on one or more robotic arms. The virtual surgical robot is built (e.g., virtually generated) from kinematic data 50. The virtual surgical robot can be rendered in a complete virtual environment including a virtual surgical robotic system such as the system shown in FIG. 1. The virtual environment can be rendered in a virtual room (e.g. a virtual operating room). The parameters for the virtual operating room (e.g. size and shape) can be provided as input or from a scan of a real physical operating room. The virtual environment can include any of the virtualized components of the surgical robotic system described in FIG. 1, such as the robotic arms, the surgical table, user console, control tower, as well as a virtual patient, and virtual assistants/personnel.

At block 94, the process includes receiving user input (e.g., through a handheld device or other sensor device) and effecting movement or configuration of the virtual surgical robot. For example, a user can use virtual touch points to arrange a surgical robotic arm in a pose. The pose can be defined based on workflow. A user can also use handheld devices to control the virtual surgical robotic arm to mimic surgery in a virtual patient. The user input can indicate a configuration of the virtual surgical robot to be generated, e.g., 2×2, 2×2 cross-under, or 3×1. For example, a 2×2 configuration can have two surgical robotic arms on opposite sides of a surgical table as shown in FIG. 1. In other embodiments, the surgical robotic arm can have three robotic arms on one side of the surgical table, and another robotic arm on the opposite side of the surgical robotic table.

Figure 5:
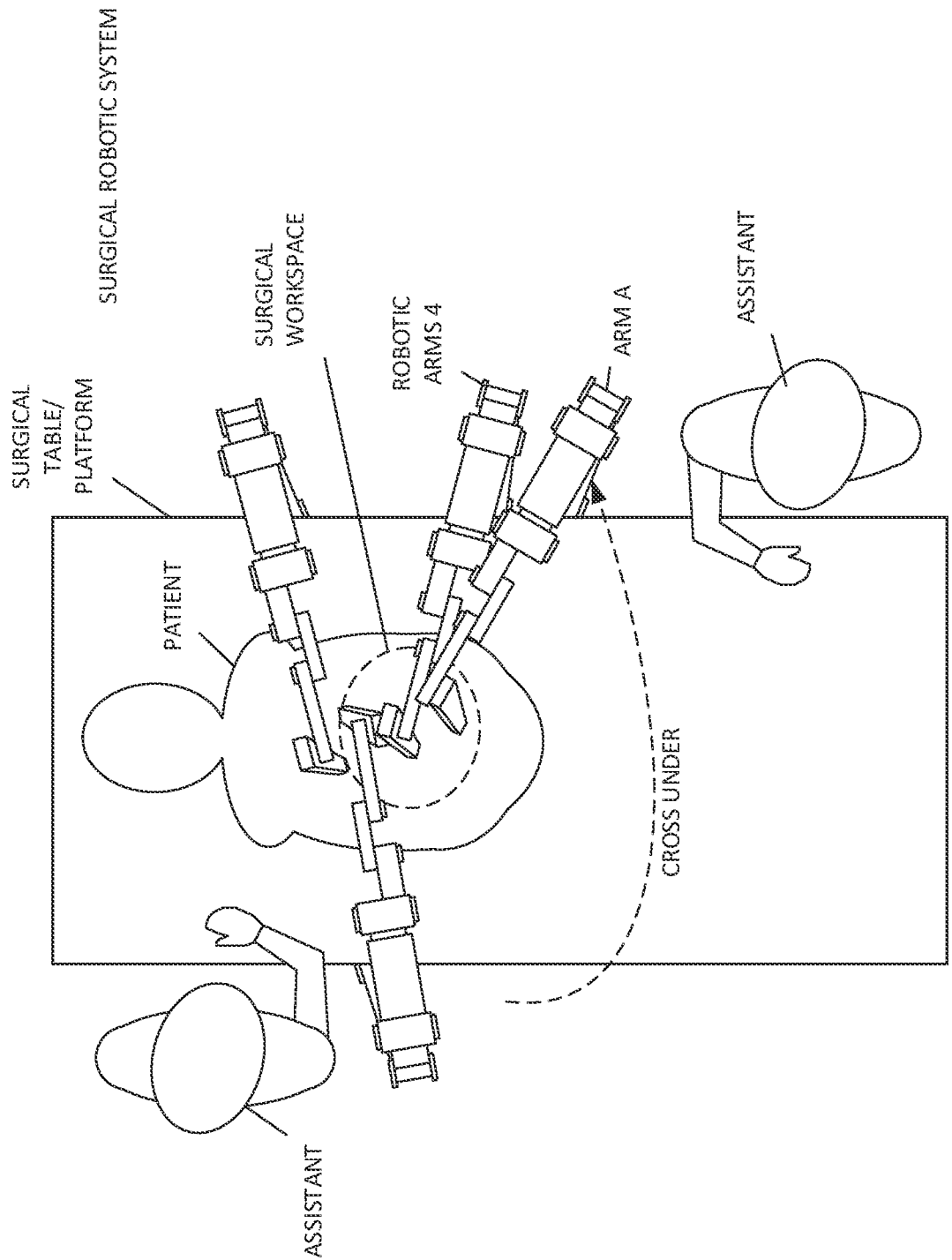
FIG. 5 shows a surgical robotic system, according to some embodiments.

FIG. 5 shows an example surgical robotic system configuration, where surgical robotic arms 4 include three arms mounted on one side of the surgical table and another arm mounted on the opposite side of the table. This arrangement can be achieved in the 2×2 cross-under configuration or the 3×1 configuration. In the 2×2 cross-under configuration, one of the surgical robotic arms (e.g., 'ARM A') can cross under the table to the opposite side, through a cross-under mechanism. The cross-under arm may have limited movement compared to the other robotic arms. In a 3×1 configuration, 'ARM A' can be removed from one side and mounted to the other side of the table by a user. Each of the different configurations, regardless of whether it be a standard 2×2, a 2×2 cross-under, or a 3×1, can be virtualized and evaluated, e.g., with respect to different workflow (required steps before, during, and after a surgical operation). The different configurations can be virtualized and evaluated.

Referring back to FIG. 3, at block 96, the process includes evaluating movement or configuration of the virtual surgical robot. As discussed, evaluation can be based one or more factors such as, but not limited to, reach or access of the virtual surgical robot (e.g., relative to a surgical workspace in a virtual patient), access of virtual personnel, or workflow with a virtual patient (e.g., evaluating whether spacing is sufficient to bring a patient onto or off the surgical table prior to and after a procedure).

Further, evaluation be based on analysis of workflow that includes set-up, or tear-down required by a surgical procedure. As described, workflow can define requirements such as poses of the surgical robots and locations and states of equipment at different stages such as prior-to, during, or after a surgical procedure. In some embodiments, collisions or the risk of collisions (near collisions) can be analyzed, such analysis being accounted for in the evaluation. Thus, the virtual surgical robot can be manipulated to try to meet the requirements of the workflow, to assess viability of the design of the surgical robot. The surgical robot can be adjusted (e.g., automatically) by modifying kinematic data of the surgical robot, based on different evaluation parameters or scores. Thus, process can provide early feedback for a surgical robotic design under different workflow and different configurations, with different patient types. Workflow limitations, reach and access, failure modes, response to complications, and collisions during regular procedures can be verified and validated before hardware development and manufacturing of a surgical robot occurs. The movements of the surgical robot form an exercises that can test one or more workflows with the surgical robot. An exercise can test for port placement, access of assistant, and/or reach and access during teleoperation of the surgical robot.

Figure 4:
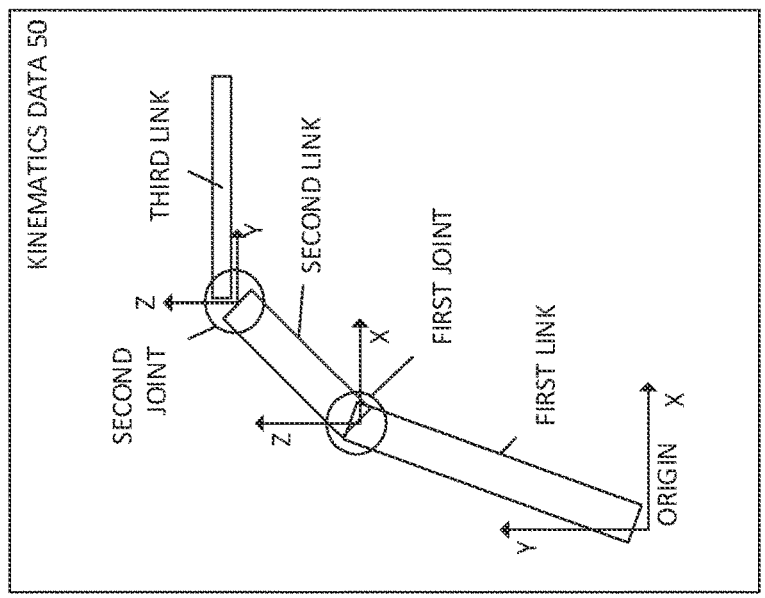
FIG. 4 shows an example of kinematic data, according to some embodiments.

At block 102, the process includes modifying the kinematics data 50, based on the evaluation. Kinematics data 50 can be stored as Unified Robot Description Format (URDF) in computer memory. FIG. 4 shows an illustrated example of kinematics data defines geometry and movement of a robot. The robotic arm can be a serial robot comprised of links and joints that are serially connected. In some embodiments, there are more links and joints present than needed to reach any point in three-dimensional space. This redundancy allows the robot to be shaped to avoid objects, e.g., the arm of a patient. Thus, modification of the virtual surgical robotic system can include adding or removing links and joints to test how different arrangements fare. Kinematics data can describe how many links a robot has, and movement constraints of each joint such as which plane and angle a joint can rotate through. Geometry such as length and width of each link can be described. Kinematics can also describe how the links are interconnected (e.g., the first link connects to the second link through the first joint). The modifying of the kinematics data can include adding or removing a link, or lengthening or shortening a link, based on the evaluation at block 96. Modifying of the kinematics data (length/shorten links, add/remove links and joints) can be performed automatically based on predefined or machine learned algorithms that receive evaluation parameters (e.g., a reach score, a stow-away score, etc.).

For example, if the evaluation shows that a port of entry or angle at port of entry at a surgical worksite could not be achieved at block 96, an additional joint and link can be added to provide an additional degree of freedom to position a surgical tool as required at the port of entry. Similarly, the evaluation can show that, with a link removed, the robot can still reach the surgical worksite sufficiently. Similarly, modifying of the kinematics data can include increasing or decreasing a length of one or more of the links based on the access or reach of the robot. Additionally, or alternatively, a user can generate user input to actively modify the kinematics data.

The virtual surgical robot can be rebuilt and rendered in real-time based on the modified kinematic data (e.g., during the same session) at block 92. The modified virtual surgical robot can then be run through the paces at block 94 and then re-evaluated at block 96, repeatedly. Thus, the process can provide continuous feedback to improve design through different workflows and configurations.

At block 104, workflow can be modified based on the simulated session that includes user movement and/or the selected configuration of the surgical robotic system. Further, workflow with respect to one or more virtual assistants 110 can be generated evaluated. Workflow can include system setup and teardown instructions, where and how system components will be arranged in the OR at different stages, draping workflow, system sterility, emergency patient access (including robotic to open/lap conversion), and arm deployment instructions.

For example, based on the virtualized environment, the system can evaluate whether assistants can stand on either side of the bed during a patient transfer, or whether an arm needs to folded in an optimal configuration to allow access to an assistant during the patient transfer. In another example, the virtualized environment can be evaluated to determine how the third arm (ARM A) is attached and covered prior to operation, or how a patient is prepped and draped, or whether the arms can sufficiently pivot in and out as required by the workflow. Evaluation can determine whether arm setup or teardown results in a potentially unacceptable workflow (e.g., based on assistant access to the patient or critical controls, spacing, or possible patient entrapment). Reach and access between the virtual assistants 110, the surgical robotic arms, and the virtual patient can be evaluated.

At block 106, the process can include modifying a control algorithm based on the evaluation. For example, the surgical robotic system can use different control algorithms to control a surgical robotic arm and/or tool based on user inputs. The control algorithms can include transformations between movements of a user input device (e.g., a handheld UID 58 in FIG. 2, or UID 14 in FIG. 1), control commands (e.g., position commands) to actuators of the surgical robotic arm, gain parameters, and damping parameters, and delays.

In some embodiments, block 98 includes storing video data of the virtual surgical environment during a training or simulation session, including movement of the virtual surgical robot. The data can be stored in computer memory such as ROM or RAM, in volatile or non-volatile memory. The stored video data can include tracked movements of the virtual surgical robotic system and/or the user (or a virtual rendering of the user) in the virtual environment.

In block 100, the process can include modifying the virtual surgical robotic system based on the stored session. The saved movements of the virtual surgical robot can be repeated or replayed with the modified kinematics data (modified at block 102). Beneficially, the same simulated session including movements of the user and the virtual surgical robot can be used to evaluate different designs of surgical robotic systems.

In one embodiment, the method includes displaying the virtual surgical environment. For example, the virtual surgical environment can be displayed to a user display on the user console (as shown in FIG. 1) or any display, local or remote. The virtual surgical environment can be displayed as a stadium view, plan view, first person view, or other view. The display can be driven by data transfer protocols between nodes (e.g., computing devices) on a network (e.g. TCP/IP, Ethernet, UDP, and more). In one embodiment, the virtual surgical environment is displayed to a head-mounted display. The wearer of the head-mounted display can be tracked such that the wearer can move throughout the virtual surgical environment to gain a three-dimensional understanding of the location and orientation of the various equipment as well as the unoccupied space and walkways within the virtual surgical environment. In one embodiment, the virtual surgical environment is interactive such that the user can adjust the orientation and/or location of objects in the virtual surgical environment (e.g., the virtual surgical robotic arm, the control tower, an angle or height of the surgical robotic platform, an angle of a display, and more).

In one embodiment, the processors of the system (for example, an optimizing processor, a kinematics processor, robot controllers, cameras, displays, and robotic arms) can include a microprocessor and memory. Each processor may include a single processor or multiple processors with a single processor core or multiple processor cores included therein. Each processor may represent one or more general-purpose processors such as a microprocessor, a central processing unit (CPU), or the like. More particularly, each processor may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Each processor may also be one or more special-purpose processors such as an application specific integrated circuit (ASIC), a cellular or base band processor, a field programmable gate array (FPGA), a digital signal processor (DSP), a network processor, a graphics processor, a communications processor, a cryptographic processor, a co-processor, an embedded processor, or any other type of logic capable of processing instructions.

Modules, components and other features, such as algorithms or method steps described herein can be implemented by microprocessors, discrete hardware components or integrated in the functionality of hardware components such as ASICS, FPGAs, DSPs or similar devices. In addition, such features and components can be implemented as firmware or functional circuitry within hardware devices; however, such details are not germane to embodiments of the present disclosure. It will also be appreciated that network computers, handheld computers, mobile computing devices, servers, and/or other data processing systems which have fewer components or perhaps more components may also be used with embodiments of the disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any particular programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A method for development of a surgical robot, comprising:
    rendering a virtual surgical robot being built from kinematic data associated with a robotic arm of the surgical robot to a display, wherein the kinematic data defines 1) movement of the robotic arm and 2) geometry of the robotic arm comprising links and joints;
    moving the virtual surgical robot based on a control algorithm and a user input; and
    revising, based on an evaluation of the moving of the virtual surgical robot,
        the kinematic data from which the virtual surgical robot is built by adjusting the geometry, wherein the revised kinematic data is to be used to increase or decrease reach or access of the robotic arm, or
        the control algorithm used to move the virtual surgical robot.

2. The method according to claim 1, wherein the virtual surgical robot includes at least one of the robotic arm, a surgical robotic table, and a surgical tool attachment on the robotic arm.

3. The method according to claim 1, wherein the evaluation is based on reach or access of the virtual surgical robot.

4. The method according to claim 1, wherein the control algorithm includes transformations between movements of a user input device.

5. The method according to claim 1, wherein the control algorithm includes position commands to actuators of the surgical robot.

6. The method according to claim 1, wherein the control algorithm includes gain parameters, damping parameters, and delays.

7. The method according to claim 1, wherein revising the kinematic data includes at least one of 1) adding or removing a link of the robotic arm and 2) adding or removing a joint of the robotic arm.

8. The method according to claim 1, wherein the kinematic data is stored in a computer readable medium in Unified Robot Description Format (URDF).

9. The method according to claim 1, wherein the virtual surgical robot has a 2×2 robotic arm configuration, a 2×2 cross-under configuration, or a 3×1 configuration.

10. The method according to claim 1, further comprising repeating the move with the virtual surgical robot, using the revised control algorithm.

11. The method according to claim 1, further comprising modifying a workflow associated with a surgical robotic procedure based on the evaluation.

12. A system for development of a surgical robot, comprising one or more processors, configured to perform the following:
    rendering a virtual surgical robot being built from kinematic data associated with a robotic arm of the surgical robot to a display, wherein the kinematic data defines 1) movement of the robotic arm and 2) geometry of the robotic arm comprising links and joints;

moving the virtual surgical robot based on a control algorithm and a user input; and revising, based on an evaluation of the moving of the virtual surgical robot, the kinematic data from which the virtual surgical robot is built by adjusting the geometry, wherein the revised kinematic data is to be used to increase or decrease reach or access of the robotic arm, or the control algorithm used to move the virtual surgical robot.

13. The system according to claim 12, wherein the virtual surgical robot includes at least one of the robotic arm, a surgical robotic table, and a surgical tool attachment on the robotic arm.

14. The system according to claim 12, wherein the evaluation is based on reach or access of the virtual surgical robot.

15. The system according to claim 12, wherein the control algorithm includes transformations between movements of a user input device.

16. The system according to claim 12, wherein the control algorithm includes position commands to actuators of the surgical robot.

17. The system according to claim 12, wherein the control algorithm includes gain parameters and damping parameters.

18. The system according to claim 12, wherein revising the kinematic data includes at least one of 1) adding or removing a link of the robotic arm and 2) adding or removing a joint of the robotic arm.

19. The system according to claim 12, wherein the kinematic data is stored in a computer readable medium in Unified Robot Description Format (URDF).

20. The system according to claim 12, wherein adjusting the geometry comprises adjusting a length of at least one link of the geometry of the robotic arm.

* * * * *